US00PP36357P2

(12) United States Plant Patent
Hansoti

(10) Patent No.: US PP36,357 P2
(45) Date of Patent: Dec. 31, 2024

(54) ***SANSEVIERIA* PLANT NAMED 'HANSOTI42'**

(50) Latin Name: *Sansevieria trifasciata*
Varietal Denomination: HANSOTI42

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 18/426,479

(22) Filed: Jan. 30, 2024

(51) Int. Cl.
*A01H 5/12* (2018.01)
*A01H 6/12* (2018.01)

(52) U.S. Cl.
USPC ..... Plt./382

(58) Field of Classification Search
USPC ..... Plt./373, 382
See application file for complete search history.

(56) References Cited

U.S. PATENT DOCUMENTS

PP33,150 P3 * 6/2021 Hansoti ..... A01H 6/12
Plt./382

* cited by examiner

*Primary Examiner* — Karen M Redden

(57) ABSTRACT

A new and distinct cultivar of *Sansevieria* plant named 'HANSOTI42' is disclosed, characterized by an extra broad, bright cream foliage margin with faint transverse banding. This brightly colored border is consistently replicated in asexually reproduced progeny. The new cultivar is a compact Birds Nest type *Sansevieria* forming small plants, reaching only about 15 to 20 cm in height at maturity. Plants require little water, having a moderate tolerance for drought, and are also tolerant of very wet conditions. Foliage is dark-green with prominent transverse bands, and bright cream-yellow margins. The new variety is a *Sansevieria*, typically produced as an indoor ornamental plant.

9 Drawing Sheets

Latin name of the genus and species: *Sansevieria trifasciata.*

Variety denomination: 'HANSOTI42'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI42'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI42' was discovered and selected by the inventor, Ashish Hansoti, as a single aberrant side shoot within a planting of *Sansevieria trifasciata* 'Hahnii Marginata', a non-patented "Hahnii" or "Birds Nest" type of *Sansevieria* grown at a nursery in Village Vangani, District Thane, Maharashtra State in Western India. 'HANSOTI42' originated as a naturally-occurring mutation of the *Sansevieria trifasciata* variety 'Hahnii Marginata' in October of 2018.

Asexual reproduction of the new *Sansevieria* cultivar by vegetative cuttings was first performed in March of 2019 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI42', which in combination distinguish this *Sansevieria* as a new and distinct cultivar:

1. Extra broad, bright cream border along the leaf margins giving a much brighter overall look to the plant. This wide border is stable and consistent on all plant material propagated from basal offshoots.
2. Occasional additional bright cream bands within the central green area of the leaf, adding to the "bright" look.
3. Other than this extra-wide border and an overall "extra bright" look, the plant is essentially identical to its parent, the typical, unpatented old open-market cultivar, *Sansevieria trifasciata* 'Hahnii Marginata'.

'HANSOTI42' has foliage variegation essentially similar to *Sansevieria trifasciata* 'Hahnii Marginata' with dark green leaves bordered with a wide band of cream but with the unique added width of this border along the edge of the leaf blade, running along the length of the leaf and occasional additional bands in the central portion of the leaf, giving a much brighter overall look to the plants.

Leaf width is quite variable and the strongest, healthiest plants have the widest leaves—this is true across all *Sansevieria trifasciata* cultivars known to the inventor. This variation means leaf width can be anything from 5 cm to 8 cm wide depending on season, growing conditions and plant vigour and plant age. Typically, the leaves are of medium width (about 6 cm average measured at the widest part of the mature leaf under good growing conditions) and lanceolate with a firm, waxy texture. The blades are thick and fleshy.

The new variety 'HANSOTI42' is a variety of *Sansevieria* in the group denominated as "Birds Nest" or 'Hahnii' types based on its origin and overall plant form. The new variety presents an average of 10 leaves per plant when it reaches maturity (about 3 months from rooted liner) but over time it can grow and accumulate many more leaves and increase in overall height.

The new variety is moderately drought tolerant and adapts well to conditions of bright light or heavy shade (exterior and interior). The intensity of leaf colour varies with exposure to light and the contrast is most intense under high light conditions.

The leaves show a variegated colouration, with a wide central area of darker green, traversed with lighter creamy cross hatching with typical *Sansevieria trifasciata* cultivars and the wide border of lighter, brighter yellowish-green.

Each leaf has a marginal cream-colored band with subtle presentation of the transverse banding seen in most *Sansevieria trifasciata* cultivars—these bands are near RHS Yellow 4B and 4C. This bright border varies in width from just 5 mm to 20 mm or even more wide. This wide creamy-yellow border is, on rare occasions, invaded with streaks of darker green from the central dark green area. This characteristic is also seen in its parental cultivar, 'Hahnii Marginata' but the width of this border band is consistently narrower.

To put it in another way, the creamy-yellow border forms 5 to 10% of the leaf width in the parent *Sansevieria trifasciata* 'Hahnii Marginata' but consistently forms 30 to 50% and sometimes even more of the width of the leaf in the invention, 'HANSOTI42'.

The central broad green area also shows alternate bands dark and light green coloration similar to RHS Green 139A and N138C, respectively. These are the usual transverse horizontal bands on the leaves typically seen in most *Sansevieria trifasciata* cultivars. In 'HANSOTI42', this green area has occasional streaks or bands of cream and this adds to the bright look of the rosette.

The backside of the leaves has similar coloration and the typical *Sansevieria trifasciata* transverse horizontal banding is very distinctly visible. These bands show alternate coloration of RHS Green 139D and 136B.

Attached colour pictures are a better guide to the overall colouration and variegation pattern rather than written descriptions. The primary distinctive characteristic is the extra-broad creamy band along the edge of each leaf, giving an overall brighter look to plants of 'HANSOTI42' compared to plants of its parent, *Sansevieria trifasciata* 'Hahnii Marginata'.

PARENTAL COMPARISON

Plants of the new *Sansevieria* 'HANSOTI42' are similar to plants of the parental cultivar, however, 'HANSOTI42' differs in the characteristics described in Table 1.

TABLE 1

| | Characteristic | Parent Cultivar 'Hahnii Marginata' | 'Hansoti42' |
|---|---|---|---|
| 1. | Leaf size | 9 to 13 cm long | 9 to 13 cm long |
| 2. | Number of leaves | 9 to 12 leaves | 10 to 13 leaves |
| 3. | Variegation Pattern | Narrow Creamy border on dark green leaves with typical *S. trifasciata* transverse banding. | Much wider, brighter creamy border than parent. Rest of the leaf is similar to parent. |
| 4. | Border Width | 2 to 12 mm | 5 to 15 mm wide |
| 5. | Central Variegation | Distinct Transverse alternate banding of dark and light grey-green as seen in most *S. trifasciata* cultivars. | Same as parent. |

COMMERCIAL COMPARATOR

Plants of the new *Sansevieria* 'HANSOTI42' are similar to the commercial variety *Sansevieria trifasciata* 'Jade Marginata', unpatented. Plants of the new *Sansevieria* 'HANSOTI42' differ from plants of the commercial cultivar in the characteristics described in Table 2.

TABLE 2

| | Characteristic | Similar Cultivar *S. trifasciata* 'Jade Marginata' | New cv 'Hansoti42' |
|---|---|---|---|
| 1. | Leaf size | 9 to 13 cm long | 9 to 13 cm long |
| 2. | Number of leaves | 9 to 12 leaves | 10 to 13 leaves |
| 3. | Variegation Pattern | Dark green whole leaf without transverse banding but with creamy border. | Much broader creamy border on dark green leaves with typical *S. trifasciata* transverse banding. |
| 4. | Border variegation | 2 to 12 mm | 5 to 15 mm wide |
| 5. | Central Variegation | None - the leaf is uniformly dark green. | Lighter transverse banding between the wide peripheral broad creamy band. |

BRIEF DESCRIPTION OF THE PHOTOGRAPHS

The accompanying photographs illustrate the overall appearance of the new *Sansevieria* cultivar 'HANSOTI42' showing the colors as true as is reasonably possible with colored reproductions of this type. Colors in the photographs may differ slightly from the color value cited in the detailed botanical description which accurately describe the color of 'HANSOTI42'.

These pictures illustrate the plant form which is the unique characteristic of 'HANSOTI42' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

DETAILED BOTANICAL DESCRIPTION

Figure 1:
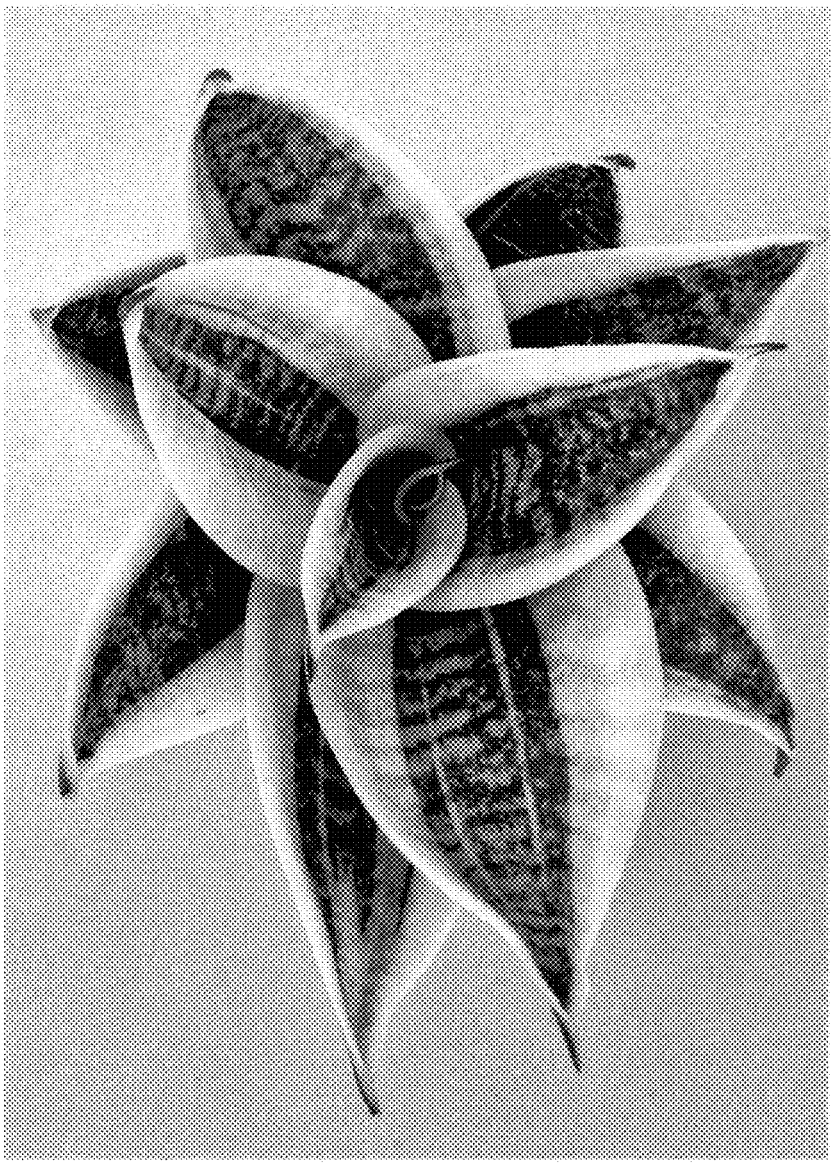
FIG. 1 shows a three-month old (from rooted liner) plant of *Sansevieria* 'HANSOTI42' in a 12 cm diameter pot.
Figure 2:
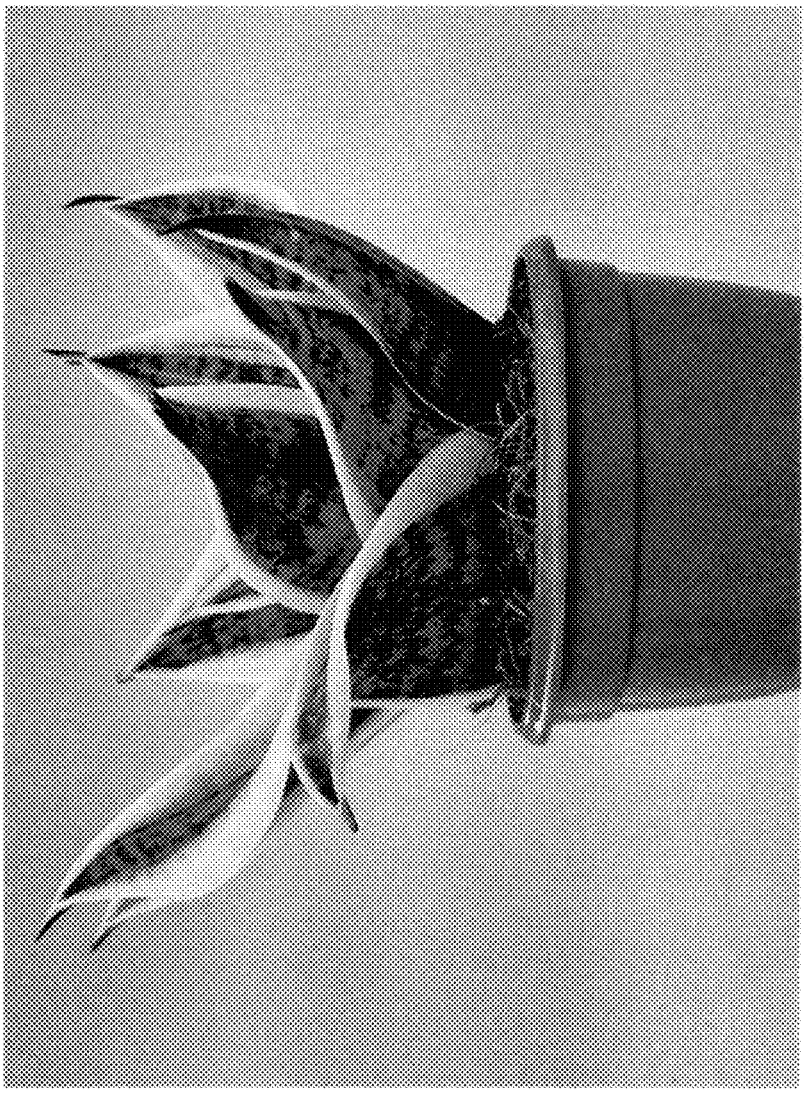
FIG. 2 is a side view of plant of 'HANSOTI42' from FIG. 1.
Figure 3:
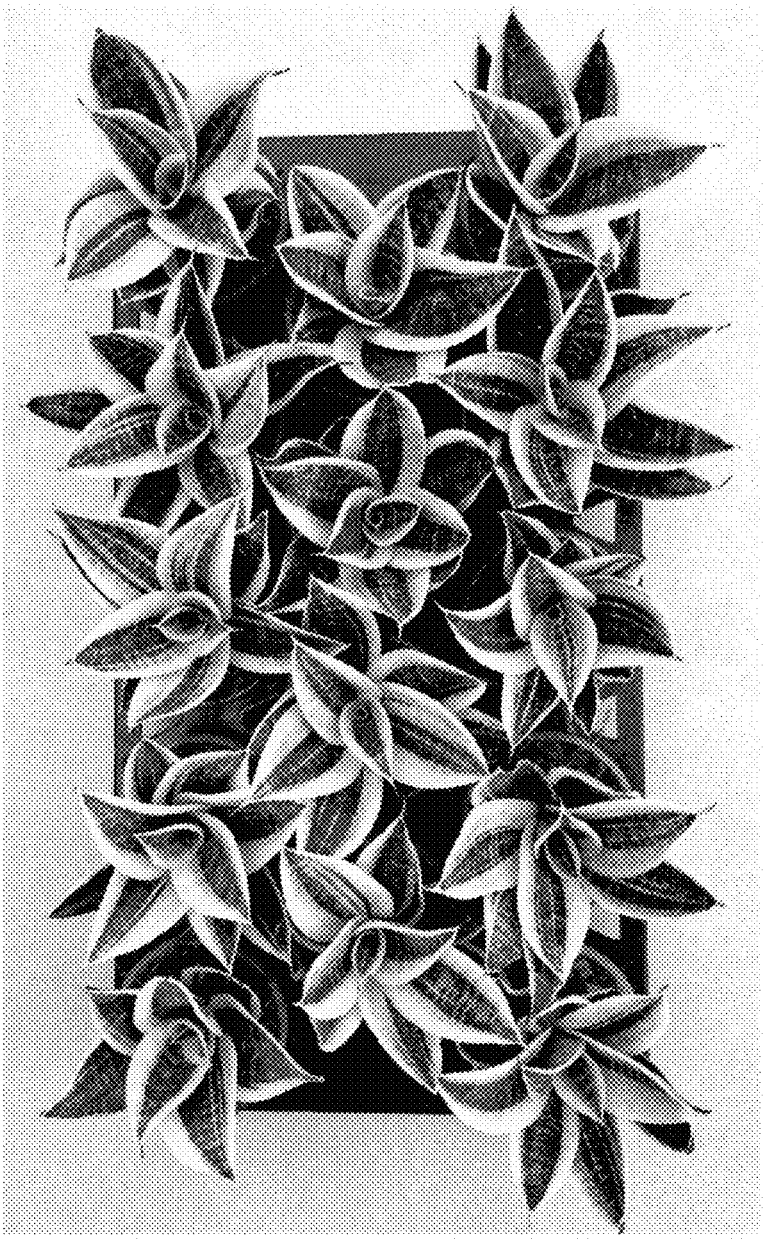
FIG. 3 Shows a group of 14 'HANSOTI42' plants in a tray, showing uniformity across multiple plants of this new cultivar.
Figure 4:
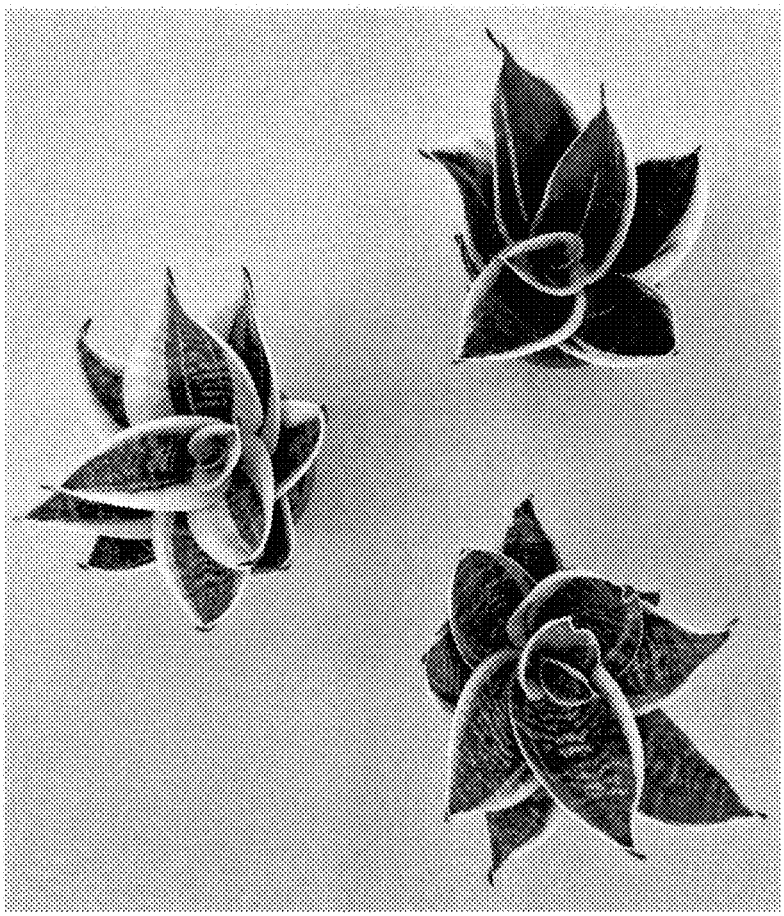
FIG. 4 is a comparator photo including the parent variety *Sansevieria trifasciata* 'Hahnii Marginata' (left) alongside a plant of the similar cultivar *Sansevieria trifasciata* 'Hahnii Jade Marginata' (right) and 'Hansoti42' (center) to compare the three.
Figure 5:
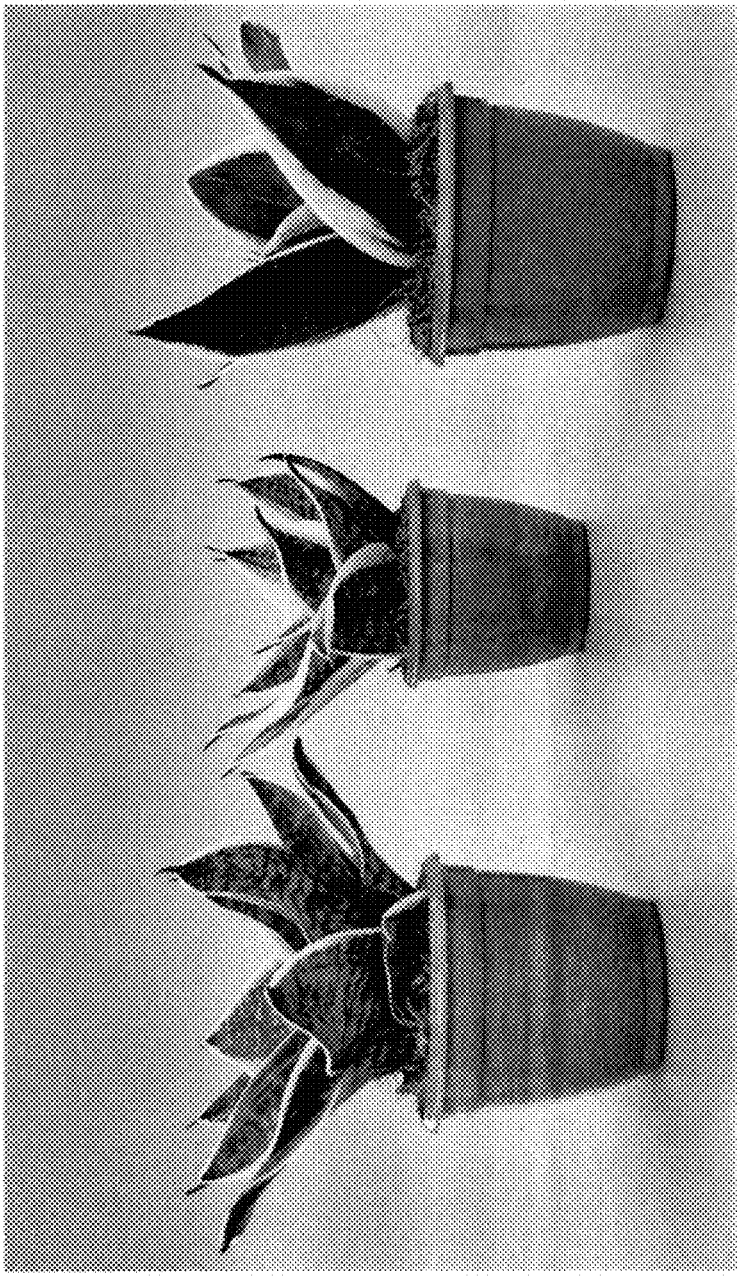
FIG. 5 is a photo of the same plants from FIG. 4 from a side view.
Figure 6:
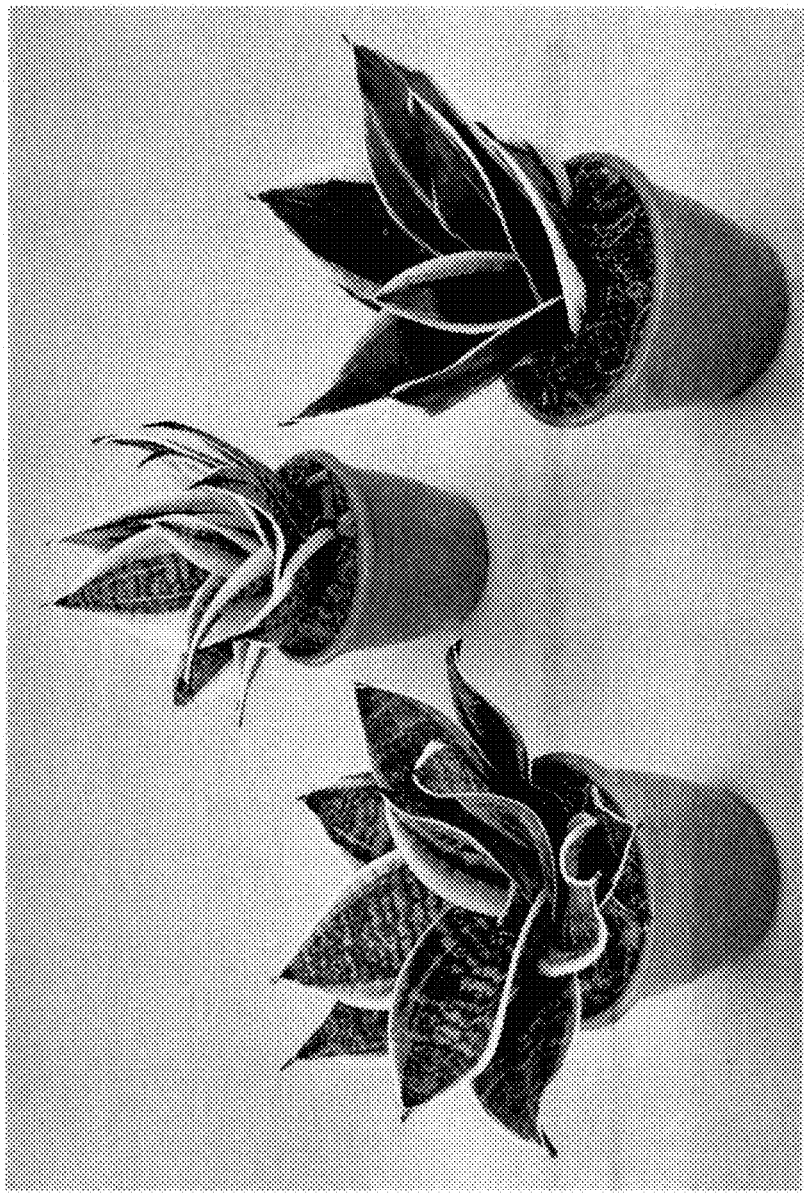
FIG. 6 is a photo of the same plants from FIGS. 4 and 5 from an upper side view which particularly depicts the foliage arrangement of the varieties.
Figure 7:
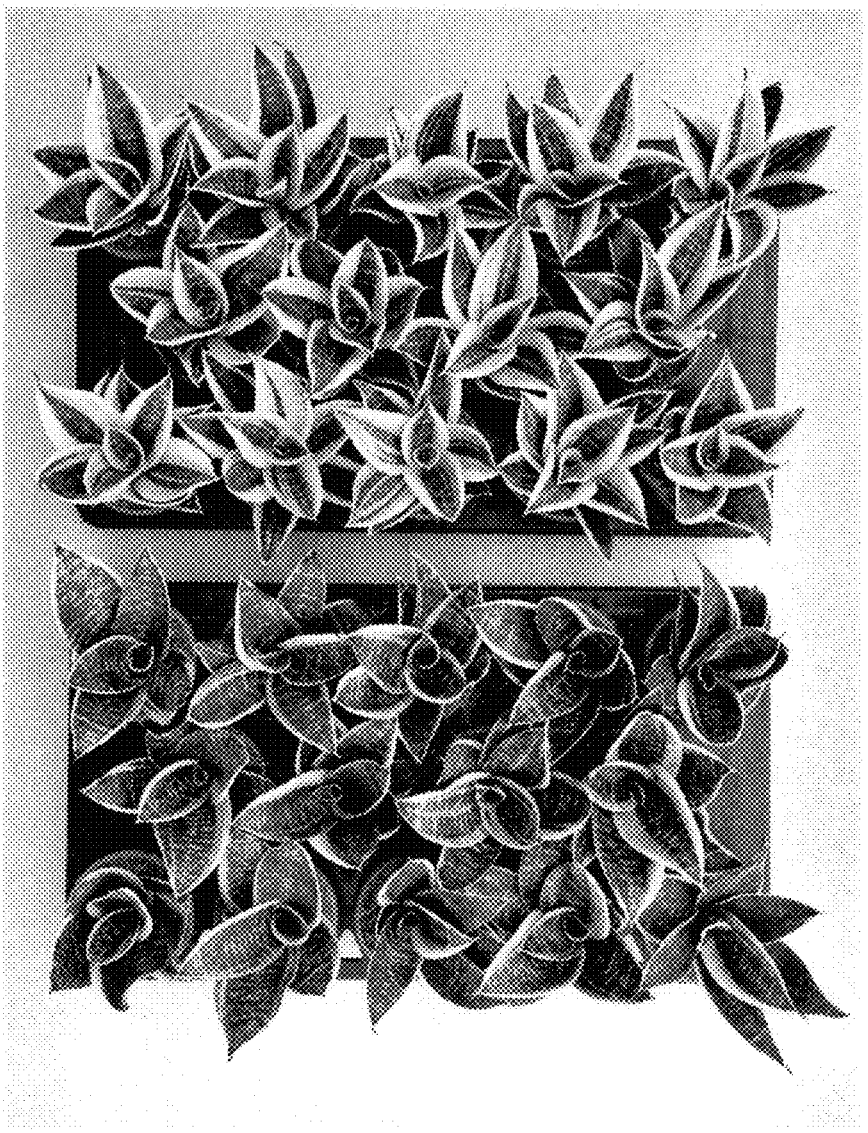
FIG. 7 shows a tray of multiple plants of the parent variety *Sansevieria trifasciata* 'Hahnii Marginata' (Top) alongside a whole tray multiple plants of the new cultivar 'HANSOTI42' (Bottom), clearly illustrating the difference in brightness and overall coloration between the two.
Figure 8:
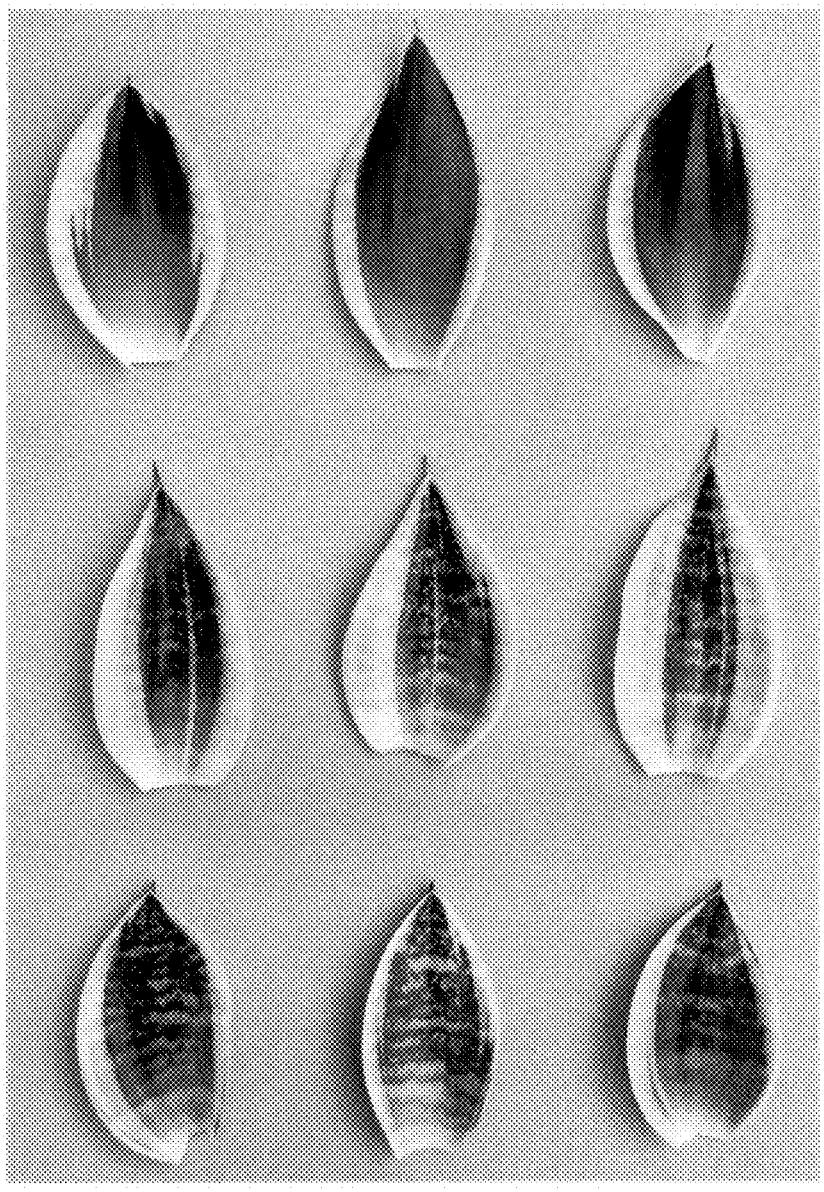
FIG. 8 shows a comparison of individual leaves of *Sansevieria* 'Hahnii Marginata', the parental variety (bottom row) and leaves of the comparable cultivar *Sansevieria trifasciata* 'Hahnii Jade Marginata' (top row) with leaves *Sansevieria* 'HANSOTI42' (center row) the novel streaking in the center of leaves of 'HANSOTI42' is very obvious. Upper leaf surfaces depicted.
Figure 9:
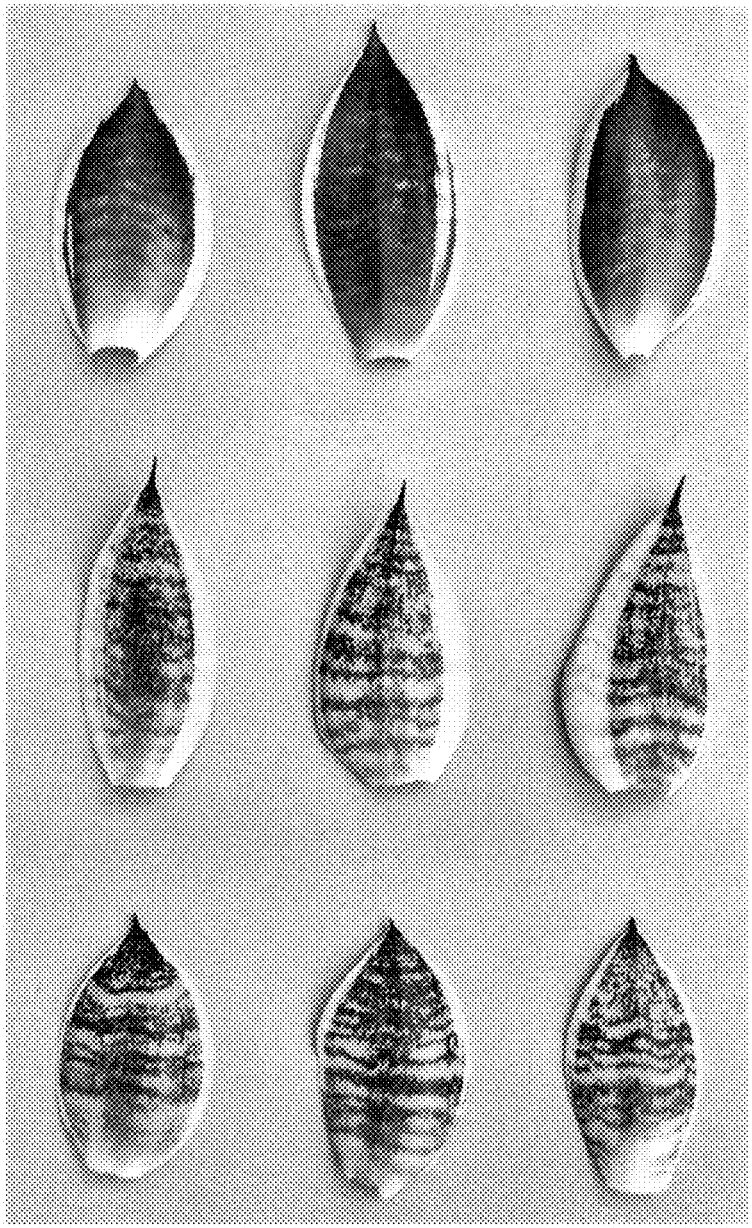
FIG. 9 shows the abaxial surface of the leaves from FIG. 8.

The new *Sansevieria* 'HANSOTI42' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI42' plants grown in an open poly house (high tunnel) at Village Asle, District Satara, Maharashtra State in Western India. Average temperature in Asle is 25° C., with summer highs of 39° C. and winter lows of 6°° C. Plants grow under natural light conditions and between 30% to 75% shade levels depending on the season (higher shade in hot summer conditions).

This crop gets nearly constant fertilization to increase production. Controlled release fertiliser of Nutricote 13:11:11 Type 360-days release at 1 kilo/cubic meter of media, Constant Liquid Feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the monsoon season in Asle, District Satara, Maharashtra State, India when outdoor day temperature was 30° C. to 38° C., and nighttime temperatures of 23° C. to 25° C. The age of the plants described is 3-4 months.

Botanical classification: *Sansevieria trifasciata* 'HANSOTI42'.

General information:

*Parentage.*—*Sansevieria trifasciata* 'Hahnii Marginata' (unpatented).

*Optimal growth conditions.*—

*Light intensities.*—High adaptability to outdoor or indoor conditions.

*Temperature.*—Day: 25° C. to 33° C. Night: 20° C. to 25° C.

*Temperature tolerance.*—Tolerant to a low temperature of about 6° C. and a high temperature of 38° C. and above — very heat tolerant.

*Fertilization.*—Constant feed of 100 ppm N, 20 ppm P and 100 ppm K is used along with micronutrients with occasional leaching.

*Growth regulators.*—Not necessary for growth, however rooting hormone aids in rapid and prolific rooting of offsets.

Propagation:

*Typical.*—Vegetative, by side suckers which come true to type. Does not come true from leaf cuttings.

*Rooting habit and description.*—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots.*—15 to 20 days at 25° C. to 30° C.

*Time to produce a rooted liner.*—About 45 days at 25° C. to 30° C.

*Time to produce ready* 12 *cm potted plant from liner.*—About 3 months at 25° C. to 30° C.

Plant:

*General appearance and form.*—Monocot; leaf bases arranged in a rosette around growth point.

*Height.*—About 12 to 15 cm when grown in 12 cm pots.

*Spread.*—About 15 to 17 cm when grown when grown in a 12 cm size container.

*Growth rate and habit.*—Moderate growth rate, stays flat and compact.

*Shape.*—Rosette.

*Fragrance.*—None.

*Stem.*—Modified (rhizomes which are fleshy with erect foliage, branching and giving offsets so forming clumps in time).

*Rosette height.*—About 12 to 15 cm height from top of pot when grown in 12 cm size container.

*Rosette diameter.*—About 15 cm to 17 cm.

*Texture.*—Smooth, waxy.

*Colour.*—As described above.

*Strength.*—Strong and durable.

*Internode length.*—About 1 mm.

Foliage:

*Quantity.*—About 9 to 12 in ready to sell plant. Number slowly increases with age.

*Arrangement and attachment.*—Single, alternate; leaf bases arranged stiffly in a rosette around central growth point.

*Leaf length.*—About 11 to 13 cm, full-size leaf.

*Leaf width.*—About 5 to 8 cm, full-size leaf.

*Overall shape of leaf.*—Lanceolate.

*Apex shape.*—Acute, triangular and aristate, with soft tip.

*Base shape.*—Plane.

*Margin.*—Sharp, smooth.

*Texture*.—Upper Surface: Smooth and waxy texture.
*Texture*.—Under Surface: Smooth and waxy texture.
*Pubescence*.—None.
*Color of mature leaf*.—Upper Surface: Basal dark green with prominent transverse bands near RHS Green 139A and N138C.
*Margins*.—Bright cream border with faint transverse banding near RHS Yellow 4B and 4C.
*Crossbanding*.—None on top surface; visible but indistinct on bottom surface of leaf.
*Color of mature leaf*.—Lower Surface: Mostly cream-yellow of RHS Yellow-Green 154B with very indistinct transverse banding of lighter than Yellow-Green 189B and with a thin dark green border along the edges of the leaf.
*Venation*.—Pattern: Longitudinal/parallel leaf shape.
*Venation color*.—Indistinguishable from leaf blade.
*Leaf fragrance*.—None.

Other:
*Inflorescence description*.—Flowers not observed to date.
*Weather resistance*.—Moderately drought tolerant.
*Pest resistance*.—Reasonably resistant to pests, susceptible to root mealybugs (*Rhizoecus pritchardi*). Typical pests include *Pseudococcidae longispinus* and *Tetranychus urticae*.
*Disease resistance*.—Occasionally shows Anthracnose and leaf spots but largely disease free from clean mother stock.
*Fruit/seed production*.—No fruits/seeds detected to date.

What is claimed is:

1. A new and distinct cultivar of *Sansevieria* plant named 'HANSOTI42' as herein illustrated and described.

* * * * *